United States Patent [19]
Tucker

[11] Patent Number: 5,718,682
[45] Date of Patent: Feb. 17, 1998

[54] ACCESS PORT DEVICE AND METHOD OF MANUFACTURE

[75] Inventor: Elton M. Tucker, Medfield, Mass.

[73] Assignee: United States Surgical Corporation, Norwalk, Conn.

[21] Appl. No.: 672,905

[22] Filed: Jun. 28, 1996

[51] Int. Cl.⁶ .................................................. A61M 11/00
[52] U.S. Cl. ........................ 604/93; 604/175; 604/244; 604/256
[58] Field of Search .................... 604/27, 28, 48, 604/49, 51, 93, 174, 175, 181, 200, 201, 244, 256, 327, 328, 890.1, 891.1; 128/899, DIG. 12

[56] References Cited

U.S. PATENT DOCUMENTS

| | | | |
|---|---|---|---|
| 4,258,711 | 3/1981 | Tucker et al. | 604/175 |
| 4,543,088 | 9/1985 | Bootman et al. | |
| 4,673,394 | 6/1987 | Fenton, Jr. et al. | |
| 4,704,103 | 11/1987 | Stöber et al. | 604/175 |
| 4,762,517 | 8/1988 | McIntyre et al. | |
| 4,772,270 | 9/1988 | Wiita et al. | 604/175 |
| 4,781,680 | 11/1988 | Redmond et al. | |
| 4,802,885 | 2/1989 | Weeks et al. | |
| 4,929,236 | 5/1990 | Sampson | |
| 5,006,115 | 4/1991 | McDonald | |
| 5,041,098 | 8/1991 | Loiterman et al. | 604/175 |
| 5,045,060 | 9/1991 | Melsky et al. | 604/891.1 |
| 5,137,529 | 8/1992 | Watson et al. | 604/891.1 |
| 5,147,483 | 9/1992 | Melsky et al. | |
| 5,213,574 | 5/1993 | Tucker | |
| 5,306,255 | 4/1994 | Haindl | |
| 5,318,545 | 6/1994 | Tucker | 604/93 |
| 5,328,465 | 7/1994 | Kratoska et al. | 604/175 |
| 5,336,194 | 8/1994 | Polaschegg et al. | |
| 5,387,192 | 2/1995 | Glantz et al. | 604/93 |
| 5,522,803 | 6/1996 | Teissen-Simony | 604/174 |

*Primary Examiner*—Mark Bockelman
*Assistant Examiner*—Bhisma Mehta

[57] ABSTRACT

A surgically implantable access port device is disclosed. The device includes a housing, a self-sealing septum, and a cup. The housing includes an internal bore leading to an upper opening, and the bore is defined by a cylindrical side wall having an inwardly protruding ledge located beneath the upper opening. The self-sealing septum is received in the bore at a location closing the upper opening and bearing against the ledge. The cup is received in the bore, and cooperates in a fixed association with the side wall of the bore to compress the septum against the ledge. The cup cooperates with the septum in defining a liquid retaining chamber. The device further includes a conduit connected to the cup and leading from the chamber to the exterior of the housing. Liquid may be injected into or removed from the chamber by penetration of the septum and passage through the conduit.

4 Claims, 3 Drawing Sheets

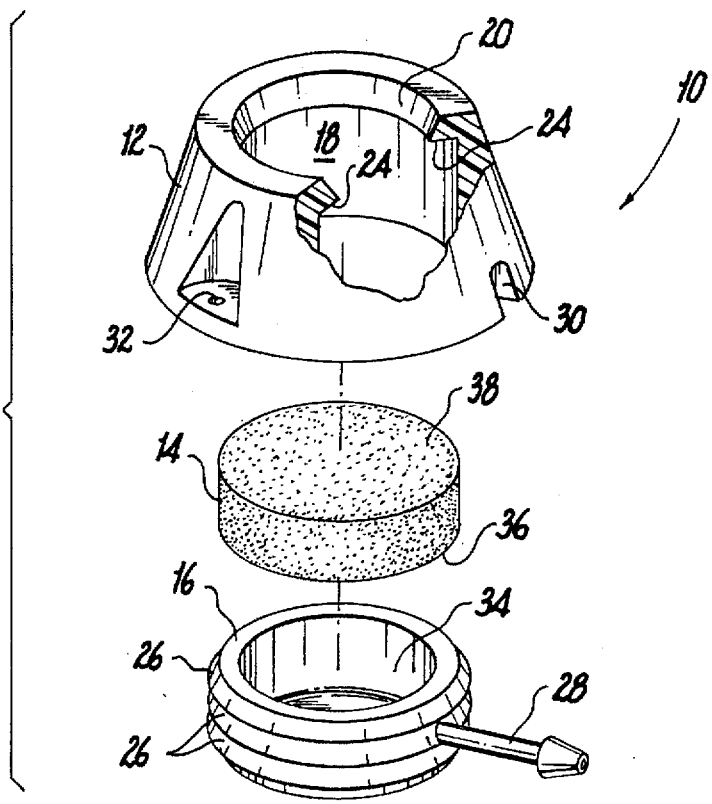
Fig. 1
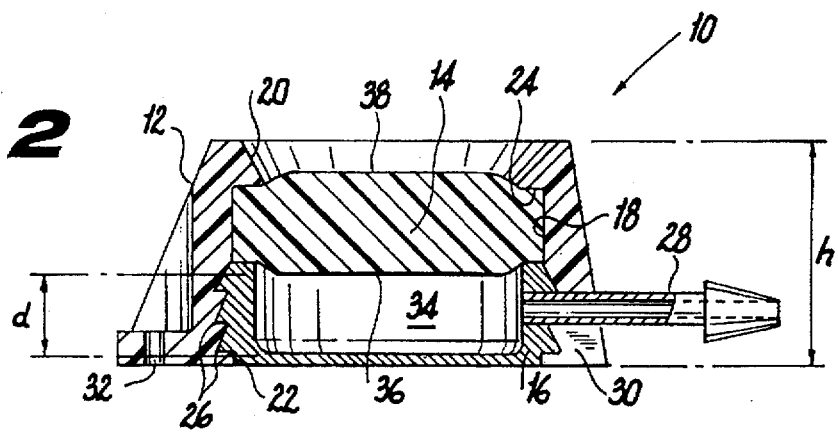
Fig. 2
Fig. 3

ACCESS PORT DEVICE AND METHOD OF MANUFACTURE

BACKGROUND

1. Technical Field

The present disclosure relates to implantable biocompatible access port devices used in the delivery of medicines, treatments, or any other fluids into a body and/or the withdrawal of fluids from a body.

2. Description of Related Art

Access port devices are surgically implanted under the skin and typically include appropriately shaped housings having internal chambers accessible via self-sealing septa. A passage in the housing communicates with the internal chamber and is connected by means of a catheter or the like to a blood vessel or other infusion site. Hypodermic needles penetrate the skin and septum to deliver medications into the internal chamber for delivery via the catheter to a selected body site. Alternatively, hypodermic needles may be employed to remove body fluids received into the internal chamber via the catheter.

It is preferable to construct access port devices from lightweight thermoplastic materials such as polyethersulfone. Certain thermoplastic materials, however, are chemically incompatible with many fluids or chemicals which may be included in medications (e.g., acetaldehyde, aniline, benzaldehyde, chlorobenzene, chloroform, phenol, pyridine and toluene). It is therefore desirable to employ an inner cup shaped element of a medication compatible material such as metal, glass or ceramic. Isolation of the fluid medication from the thermoplastic housing is achieved by maintaining a tight sealing engagement between the self-sealing penetrable septum and the cup shaped element.

Present techniques for assembling such multicomponent access port devices typically involve bonding or fastening together a multicomponent housing assembly that sandwiches the cup element and the septum. For example, as discussed in U.S. Pat. Nos. 5,213,574 and 5,318,545, the disclosures of which are hereby incorporated by reference, a conventional multicomponent access port device incorporating an inner cup shaped element typically includes a thermoplastic housing formed of two housing components that sandwich a septum and a cup shaped element.

It is desirable that the access port device have as small an overall height as possible yet define an internal chamber within the cup having as large a depth as possible. Access port devices having lower overall heights are desired for use with smaller patients such as children, and provide increased comfort to most patients. Since the outlet openings on many types of needles are along the side walls thereof and are set back from the tip, the internal chamber must be of a sufficient depth to permit the side opening of larger needles (which may be required in certain applications) to be fully inserted into the internal chamber. If the side opening of the needle does not enter the chamber and instead remains within the septum, then fluid introduction into the chamber may be impeded or blocked entirely.

A principal objective of the present disclosure is to provide an access port device having an increased ratio of internal chamber depth to overall height such that the depth of the chamber may be optimized with respect to the overall height.

Companion objectives include either reducing the overall height of the device without decreasing the depth of the internal chamber, or alternatively maximizing the depth of the internal chamber without increasing the overall height of the device.

SUMMARY

The surgically implantable access port device disclosed herein includes a housing, a self-sealing septum, and a cup. The housing includes an internal bore leading to an upper opening, and the bore is defined by a cylindrical side wall having an inwardly protruding ledge located beneath the upper opening. The self-sealing septum is received in the bore at a location closing the upper opening and bearing against the ledge. The cup is received in the bore, and cooperates in a fixed association with the side wall of the bore to compress the septum against the ledge. The cup cooperates with the septum in defining a liquid retaining chamber. The device further includes a conduit connected to the cup and leading from the chamber to the exterior of the housing. Liquid may be injected into or removed from the chamber by penetration of the septum and passage through the conduit.

In one embodiment, the cup is fixed to the cylindrical side wall of the housing by including radially outwardly projecting teeth integral with the cup that engage the cylindrical side wall. In another embodiment, the cup is fixed to the cylindrical side wall by including an oversized band or ring on the outer wall of the cup that engages the cylindrical side wall of the housing and is preferably thereafter welded to the housing.

BRIEF DESCRIPTION OF THE DRAWINGS

The following description of preferred embodiments will be further understood with reference to the accompanying drawings in which:

FIG. 1 is an exploded isometric view of an access port device in accordance with one embodiment of the disclosure;

FIG. 2 is a partial sectional view of the assembled access port device shown in FIG. 1;

FIG. 3 is a partial sectional view similar to that shown in FIG. 2 of an assembled access port device in accordance with another embodiment of the invention;

DETAILED DESCRIPTION OF THE ILLUSTRATED EMBODIMENTS

As shown in FIGS. 1 and 2, an access port device 10 in accordance with a first embodiment of the disclosure includes a unitary housing 12 formed of a biocompatible material such as polyethersulfone or any other suitable plastic, a septum 14 formed of a suitable self-sealing penetrable material such as silicone rubber, and a cup 16. The cup 16 may be formed in whole or in part of various non-reactive materials such as metals (e.g., titanium and stainless steel), glass or ceramics (e.g., alumina ceramics ($Al_2O_3$) or zirconia ceramics ($Y_2O_3$- yttria-partially stabilized zirconia as sold by Coors Ceramics Company in Golden, Colo.).

Figure 7:
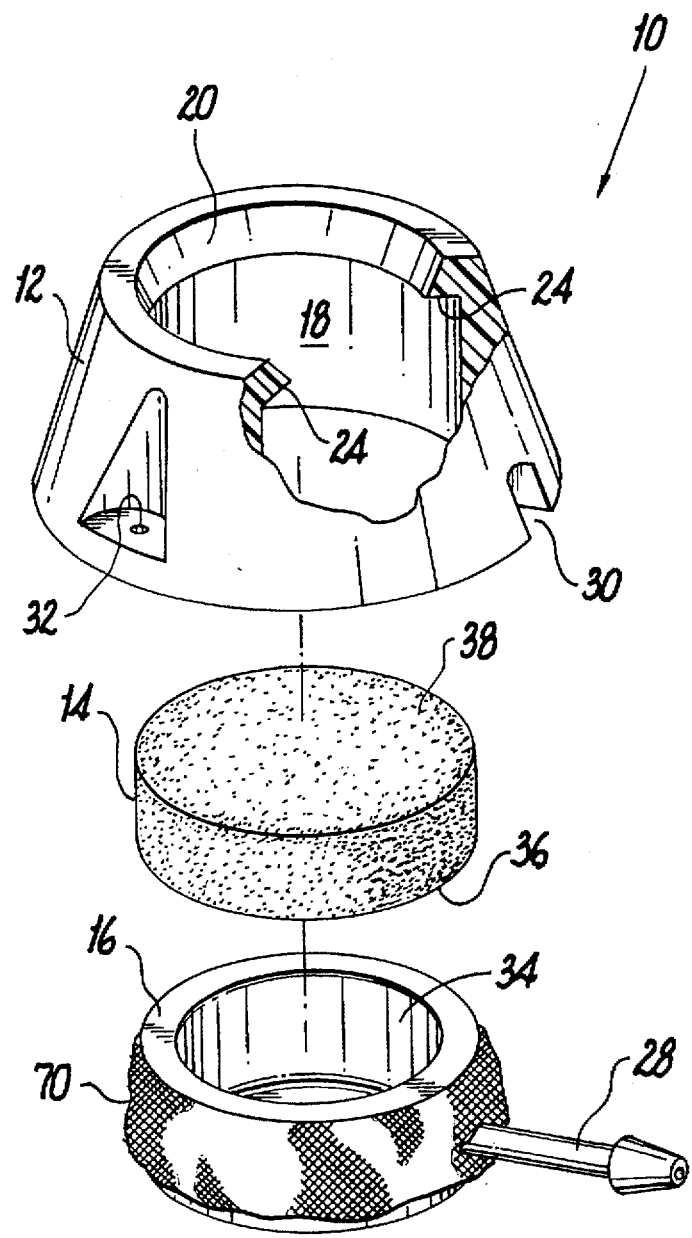
FIG. 7 is an exploded isometric view of an access port device in accordance with a second embodiment of the disclosure.

The housing 12 includes an internal bore 18 extending between a top opening 20 and a bottom opening 22, as well as an internal ledge 24 within the bore 18 near the top opening 20. The septum 14 is sized to fit through the bottom opening 22 and be received within the bore 18 against the ledge 24 as shown in FIG. 2. The cup 16 is formed with radially outwardly projecting teeth or circular barbs 26. Alternatively or in addition, the outside surface of cup 16 may be knurled or otherwise texturized. A cup having a knurled surface 70 is shown by FIG. 7, where identical reference numerals designate similar structure as the access port device 10 shown by FIG. 1. The barbs 26 may be formed integral with the cup. The outer diameter of the barbs 26 is larger than the inner diameter of the bore 18. An outlet tube 28 of a non-reactive material, preferably similar to that of the cup 16, is attached at 29.

During assembly, the septum 14 and cup 16 are introduced into the housing 12 through the bottom opening 22. Since the outer diameter of the cup barbs 26 exceeds the inner diameter of the bore 18, the cup 16 must be pressed into the housing 12. As the cup 16 is pressed into the housing 12, it compresses the septum 14 against the ledge 24. The barbs 26 penetrate radially into the wall of the bore 18 and thus act to secure the cup 16 to the housing 12. The neck of the outlet tube 28 is received within a U-shaped notch 30 in the housing 12.

The interference fit between the inner bore 18 of the housing 12 and the barbs 26 of the cup 16 may be achieved in numerous ways. For example, the cup 16 may be mechanically or hydraulically pressed into the housing until it contacts and compresses the septum to create a fluid tight enclosure for liquid received in the chamber 34. Due to the interference fit between the non-plastic barbs 26 and the plastic housing 12, the plastic will flow around and surround the barbs 26. During assembly, the cup 16 may be subjected to vibration at ultrasonic frequencies either during and/or following mechanical compression. The vibration causes the plastic material at the cup interface to become molten and more quickly and more completely flow around the barbs 26 to mechanically lock the compressed components together. Alternatively, the plastic housing may be molded around the cup. In all cases, the housing 12 and cup 16 are firmly held together following assembly so as to maintain compression of the septum 14 between the cup 16 and the inner housing ledge 24, thereby providing a tightly sealed inner chamber 34.

The inner chamber 34 is defined in part by the inner surface 36 of the septum 14 as shown in FIG. 2. Although the inner surface 36 may become curved when the septum and cup are compressed together as shown, the depth "d" as depicted in FIG. 2 is shown for illustrative purposes to generally indicate the average depth of the inner chamber 34. The depth "d" of the inner chamber 34 may be increased without increasing the overall height "h" of the access port device since the housing is not required to sandwich the cup and septum. Similarly, the height "h" of the device may be decreased without requiring that the depth "d" of the inner chamber 34 be decreased. The bottom of the cup 16 is preferably flush with the bottom of the housing 12 following assembly as shown in FIG. 2. In other embodiments, the bottom of the access port device may include a lower housing portion that either partially or completely covers the bottom of the cup.

During use, the access port device 10 is surgically implanted under a patient's skin and is typically secured to fascia underlying the skin by means of sutures threaded through peripheral apertures 32. The outlet tube 28 is suitably adapted for connection to a catheter or other like delivery conduit within the patient's body. The outer surface 38 of the septum 14 is exposed through the top opening 20 of the housing 12, and fluid medications may be injected via a hypodermic needle through the skin and septum 14 into the chamber 34. The septum 14 automatically reseals itself after having been penetrated by the needle, and the chamber 34 serves as a conduit permitting fluid medications to be introduced into the patient's body via the outlet tube 28. The access port device also may be used to similarly withdraw body fluids (e.g., blood) from the patient's body.

Figure 4:
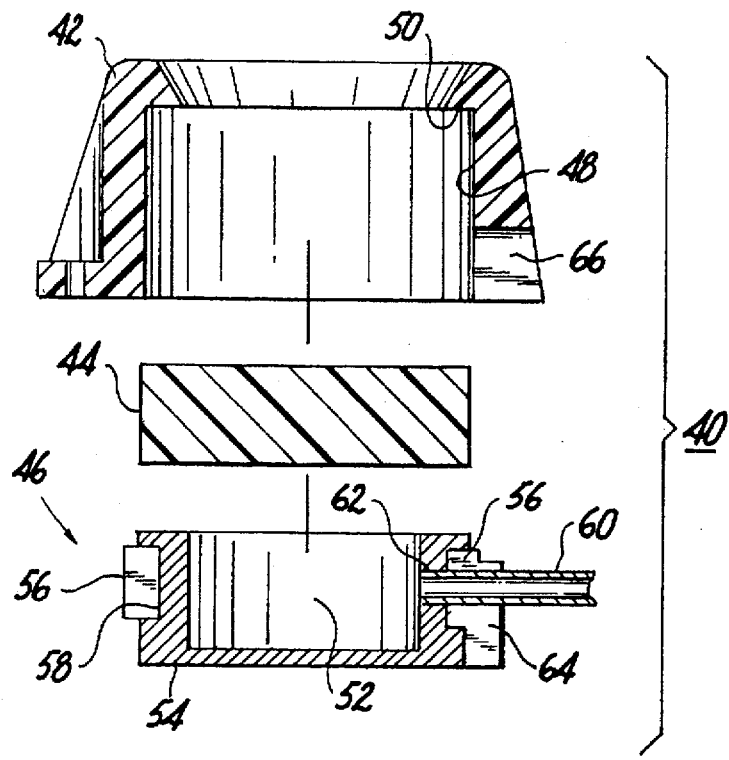
FIG. 4 is an exploded sectional view of the access port device shown in FIG. 3.

As shown in FIGS. 3 and 4, another embodiment includes an access port 40 having a unitary plastic housing 42, a self-sealing penetrable septum 44 and a multi-component cup unit 46. The cup unit 46 and septum 44 are similarly received within a bore 48 within the housing 42 to compress the septum 44 against a ledge 50 and define a fluid tight inner chamber 52.

Figure 5:
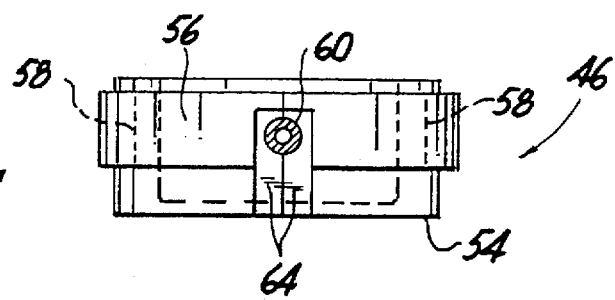
FIG. 5 is a side elevational view of the access port cup shown in FIG. 4.
Figure 6:
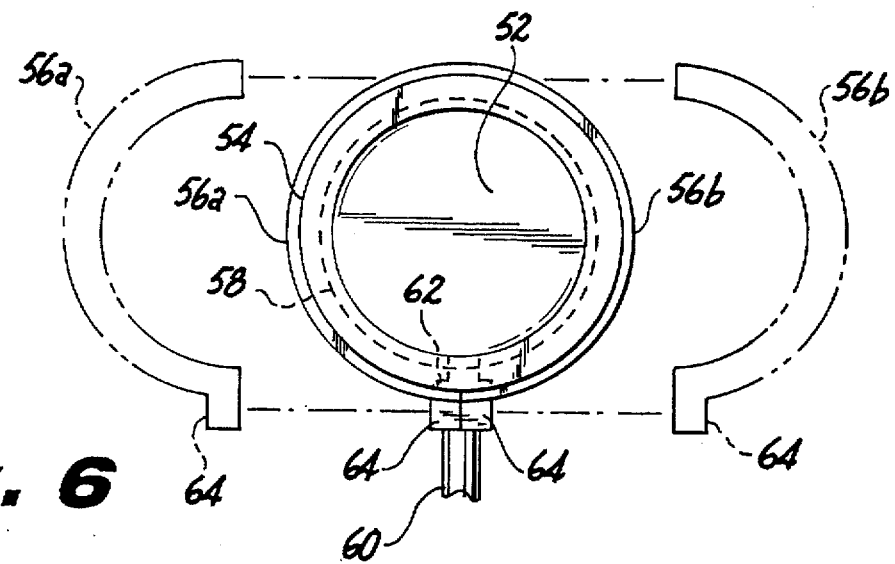
FIG. 6 is a top plan view of the access port cup shown in FIG. 5 with the cup ring thereof shown in an exploded view in phantom.

As shown in FIGS. 5 and 6 the multi-component cup unit 46 includes a metallic or ceramic cup shaped element 54 and a plastic cup ring 56 that is formed of two ring halves 56a, 56b that together encircle the cup element 54. The outer diameter of the cup ring 56 is larger than the inner diameter of the bore 48 in the housing 42, and the interference fit achieved upon pressing the cup unit 46 into the housing 42 will serve to lock the components together while compressing the septum 44 against the ledge 50. The cup ring 56 is secured from axial movement by being partially received within an annular recess 58 in the outer wall of the cup element 54 as shown in FIGS. 3–6.

During a preferred assembly procedure, the septum 44 is inserted into the housing 42 and the two components are held in a fixed position. The cup ring halves 56a, 56b are brought together around the cup shaped element 54 and the thus formed cup unit 46 is then inserted into the lower opening in the housing 44. The components are mechanically compressed together while the bottom of the cup element 54 is subjected to vibration at ultrasonic frequencies. The resulting heat generated between the plastic cup ring halves 56a, 56b and the plastic housing 42 causes each of the plastic materials to melt at their interfaces which permanently welds the three plastic components together.

Prior to assembly, the cup element 54 is attached to an outlet tube 60. The cup ring halves 56a, 56b capture opposite side portions of the outlet tube 60 as shown in FIGS. 5 and 6. The cup ring halves 56 further include portions 64 that fill a significant portion of the rectangular opening 66 in the housing 42 into which the outlet tube 60 is received. A washer element 62 between the cup element 54 and the cup ring 56 holds the outlet tube 60 in place.

Those skilled in the art will appreciate that numerous modifications may be made to the above described embodiments without departing from the spirit and scope of the claimed invention.

What is claimed is:

1. A surgically implantable device comprising:
   a housing including an internal bore leading to an upper opening, said bore being defined by a cylindrical side wall having an inwardly protruding ledge located beneath said upper opening, said housing being molded of a plastic material;
   a self-sealing septum received in said bore at a location closing said upper opening and bearing against said ledge;
   a cup received in said bore and being in mechanical interengagement with said side wall, said cup cooperating in a fixed association with the side wall of said bore to compress and fix said septum against said ledge and to cooperate with said septum in defining a liquid retaining chamber, said cup comprises a non-plastic material with external means for projecting radially outwardly into the side wall of said bore, said external means comprising a plurality of teeth for engaging said cylindrical side wall of said housing; and a conduit connected to said cup and leading from said chamber to the exterior of said housing, whereupon liquid may be caused to flow into or from said chamber through said conduit.

2. The surgically implantable device of claim 1, wherein said plurality of teeth are formed integral with said cup.

3. A surgically implantable device comprising:

a housing including an internal bore leading to an upper opening, said bore being defined by a cylindrical side wall having an inwardly protruding ledge located beneath said upper opening, said housing being molded of a plastic material;

a self-sealing septum received in said bore at a location closing said upper opening and bearing against said ledge;

a cup received in said bore and being in mechanical interengagement with said side wall, said cup cooperating in a fixed association with the side wall of said bore to compress and fix said septum against said ledge and to cooperate with said septum in defining a liquid retaining chamber, said cup comprises a non-plastic material with external means for projecting radially outwardly into the side wall of said bore, said external means comprising a plurality of non-plastic barb rings encircling an outer wall of said cup for engaging said cylindrical side wall of said housing; and a conduit connected to said cup and leading from said chamber to the exterior of said housing, whereupon liquid may be caused to flow into or from said chamber through said conduit.

4. A surgically implantable access port device comprising:

a housing formed of a thermoplastic material and including an internal bore leading to an upper opening, said bore being defined by a cylindrical side wall having an inwardly protruding ledge located beneath said upper opening;

a non-thermoplastic cup received within said bore, said cup including a side wall and an upper portion, and defining an internal chamber in fluid communication with a conduit extending to the exterior of said housing;

a self-sealing septum compressed between said upper portion of said cup and said ledge within said housing, at least a portion of said septum being exposed through said upper opening in said housing and permitting the passage of a needle therethrough; and securing means associated with said side wall of said bore and side wall of said cup, said securing means comprises a plurality of non-thermoplastic barbs on an outer circular wall of said cup, said barbs being adapted to engage said cylindrical wall of said housing for securing at least a portion of said cup side wall with at least a portion of said cylindrical side wall of said housing for limiting the movement of said cup with respect to said housing.

* * * * *